(12) United States Patent
Chobotov

(10) Patent No.: US 6,331,191 B1
(45) Date of Patent: Dec. 18, 2001

(54) LAYERED ENDOVASCULAR GRAFT

(75) Inventor: Michael V. Chobotov, Santa Rosa, CA (US)

(73) Assignee: TriVascular Inc., Santa Rosa, CA (US)

( * ) Notice: Subject to any disclaimer, the term of this patent is extended or adjusted under 35 U.S.C. 154(b) by 0 days.

(21) Appl. No.: 09/200,317

(22) Filed: Nov. 25, 1998

Related U.S. Application Data

(60) Provisional application No. 60/066,301, filed on Nov. 25, 1997.

(51) Int. Cl.$^7$ ........................................................ A61F 2/00
(52) U.S. Cl. ............................................ 623/1.44; 623/1.21
(58) Field of Search .................................... 623/1, 11, 12, 623/1.15, 1.16, 1.21, 1.27, 1.44

(56) References Cited

U.S. PATENT DOCUMENTS

| 5,562,724 | * | 10/1996 | Vorwerk | 623/1 |
| 5,662,675 | | 9/1997 | Stockert et al. | 606/194 |
| 5,667,523 | * | 9/1997 | Bynon | 606/198 |
| 5,755,772 | * | 5/1998 | Evans | 623/1 |
| 5,843,160 | * | 12/1998 | Rhodes | 623/1 |
| 5,916,264 | * | 6/1999 | Von Oepen | 623/1 |
| 6,102,918 | * | 8/2000 | Kerr | 606/108 |

FOREIGN PATENT DOCUMENTS

| 0792627A2 | | 3/1997 | (EP) . |
| 92/00043 | * | 1/1992 | (WO) | 623/1 |

\* cited by examiner

Primary Examiner—Michael J. Milano
(74) Attorney, Agent, or Firm—William B. Anderson; Heller Ehrman White & McAuliffe

(57) ABSTRACT

A endovascular graft having at least two thin wall graft members, with at least one of the thin wall graft members configured to be deployed within a lumen of another thin wall graft member. The thin wall graft members may be coupled or connected to each other so as to allow relative axial displacement of the sections, or they may be separate members that have dimensions and a configuration to allow coaxial deployment within inner lumens of each other. By having multiple thin wall graft member, the graft may be built up within a patient's vasculature in steps through a delivery catheter system that is smaller in profile and more flexible than a delivery catheter system configured to deliver a single component graft. The graft of the invention may be delivered percutaneously or intraoperatively.

22 Claims, 3 Drawing Sheets

LAYERED ENDOVASCULAR GRAFT

RELATED APPLICATIONS

This application is a continuation-in-part of Provisional Application Serial NO. 60/066,301, filed Nov. 25, 1997. Priority is hereby claimed to Provisional Application Serial No. 60/066,301, which also incorporated by reference in its entirety herein.

BACKGROUND OF THE INVENTION

The present invention relates to a system and method for the treatment of disorders of the vasculature. More specifically, the present invention relates to a system and method for treatment of thoracic or abdominal aortic aneurysm and the like, which is a condition manifested by expansion and weakening of the aorta. Such conditions require intervention due to the severity of the sequelae, which frequently is death. Prior methods of treating aneurysms have consisted of invasive surgical methods with graft placement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures have a high mortality rate due to the possibility of the rupture discussed above in addition to other factors. Such other factors can include poor physical condition of the patient due to blood loss, anuria, and low blood pressure associated with the aortic abdominal aneurysm. An example of a surgical procedure is described in a book entitled *Surgical Treatment of Aortic Aneurvsms* by Denton A. Cooley, M.D., published in 1986 by W. B. Saunders Company.

Due to the inherent risks and complexities of surgical procedures, various attempts have been made in the development of alternative methods for deployment of grafts within aortic aneurysms. One such method is the non-invasive technique of percutaneous delivery by a catheter-based system. Such a method is described in Lawrence, Jr. et al in "Percutaneous Endovascular Graft: Experimental Evaluation", *Radiology* (May 1987). Lawrence described therein the use of a Gianturco stent as disclosed in U.S. Pat. No. 4,580,568. The stent is used to position a Dacron® fabric graft within the vessel. The Dacron® graft is compressed within the catheter and then deployed within the vessel to be treated. A similar procedure has also been described by Mirich et al. in "Percutaneously Placed Endovascular Grafts for Aortic Aneurysms: Feasability Study", *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery catheters used to deliver the grafts are relatively large in profile, often up to 24 French and greater, and stiff in bending. The large profile and bending stiffness makes delivery through the irregular and tortuous arteries of diseased vessels difficult and risky. In particular, the iliac arteries are often too narrow or irregular for the passage of a percutaneous device. In addition, current devices are particularly challenged to reach the deployment sizes and diameters required for treatment of lesions in the aorto and aorto-iliac regions. Because of this, non-invasive percutaneous graft delivery for treatment of aortic aneurysm is not available to many patients who would otherwise benefit from it.

While the above methods have shown some promise with regard to treating thoracic and abdominal aortic aneurysms with non-invasive methods, there remains a need for an endovascular graft system which can be deployed percutaneously in a small diameter flexible catheter system. The present invention satisfies these and other needs.

SUMMARY OF THE INVENTION

The present invention is directed generally to a system and method for treatment of a body lumen or passageway within a patient's body. More specifically, the invention is directed to an endovascular graft for treatment of weakened or diseased blood vessels which has at least two thin wall graft members which are configured to be nested or layered over each other in a deployed state. By layering a plurality of thin wall graft members, each layer can be delivered by a smaller more flexible catheter delivery system than is used for conventional single graft systems. The system of the present invention may delivered intraoperatively, but is preferably delivered percutaneously.

One embodiment of the invention is a graft for supporting a preselected length of a patient's body lumen or passageway that is created from at least two separate thin wall graft members. The thin wall graft members are configured to be nested or layered when deployed in an overlapping fashion that combines the strength of the members in the areas or portions that are overlapped. One advantage of such a system and method is that each individual thin wall graft member can be constructed with less bulk and material mass than would be required for a single component graft of similar strength. This allows each separate thin wall graft member to have a smaller more flexible profile in a compressed or constricted state and be deliverable through a smaller and more flexible delivery system which improves access to preselected lengths of compromised or diseased body lumens.

The graft can be configured so that no single component or thin wall graft member has sufficient mechanical strength to provide a desired amount of support for a preselected length of a patient's body lumen. The thin wall graft members can be designed so that a desired amount of mechanical strength can be achieved with two or more layers or overlapped portions of the graft. In some indications, it may be desirable to have three, four, five or more layers required to achieve the desired amount of mechanical strength and support for the patient's body lumen. While a graft requiring more layers for sufficient strength may be more time consuming to deploy, each thin wall graft member or component can be made correspondingly thinner and with a lower more flexible profile in a constrained or compressed state. This allows a correspondingly smaller and more flexible catheter delivery system to be used to access the preselected length of body lumen to be treated.

In some embodiments, it may be preferable to have the inner-most and lastly deployed thin wall graft member be of a longitudinal length greater than the previously deployed thin wall graft members, individually, or cumulatively as deployed. In this way, the lastly deployed thin wall graft member can extend longitudinally from one or both ends of the graft and provide a smooth transition into the graft for blood flow and a smooth inner surface for the graft in its final deployed state.

Generally it is desirable for the preselected length of a patient's body lumen which is compromised or requires treatment to be completely spanned by at least the number of thin wall graft members required to achieve a desired amount of mechanical strength and support. In this way, each thin wall graft member that provides a portion of the requisite desired strength can be anchored with appropriate anchoring mechanisms in tissue that is healthy or of sufficient integrity to be capable of supporting the anchoring mechanisms. Each thin wall graft member is typically equipped with at least one anchoring mechanism at each end to prevent the thin wall graft member from being displaced from the deployment site and to facilitate sealing of the graft member against an inside surface of the patient's body lumen or vessel.

In an alternative embodiment of a graft of the present invention, thin wall graft members are linked to allow relative longitudinal movement or displacement of the members. In a preferred embodiment, each thin wall graft member is connected to an adjacent member in a telescopic manner. This allows the graft members to be extended longitudinally so that only one thickness of graft member need be compressed or constrained for loading of the graft into a delivery catheter system, except for the short lengths of overlapped portion where the ends of the thin wall graft members are joined. This provides some of the advantages of the separate individually deliverable thin wall graft members while maintaining an integral structure. The telescoping graft can be deployed by positioning each thin wall graft member within an adjacent thin wall graft member after exiting the distal end of the delivery catheter system. The graft is then expanded as a whole at a preselected site within the patient's body lumen. Alternatively, the graft may be deployed one thin wall graft member at a time, with each graft member deployed and expanded radially in a desired position as it exits the delivery catheter system.

These and other advantages of the invention will become more apparent from the following detailed description of the invention when taken in conjunction with the accompanying exemplary drawings.

DETAILED DESCRIPTION

Figure 1:
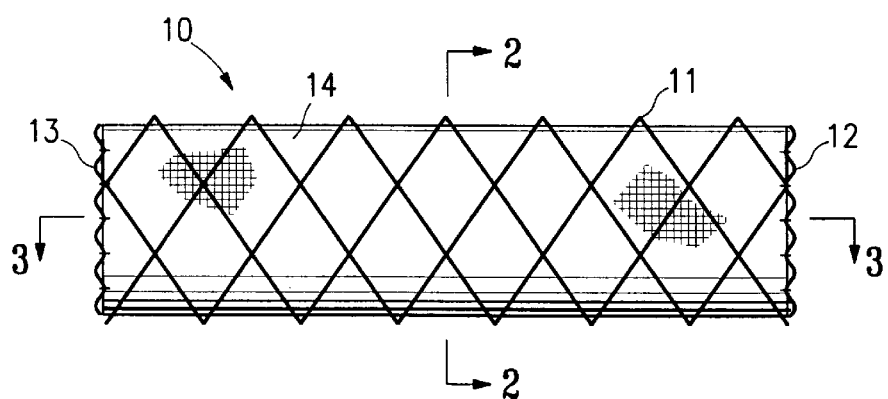
FIG. 1 shows an elevational view of an endovascular graft having features of the invention.

An endovascular graft having features of the invention allows for minimally invasive surgical repair or treatment of aneurysms, arteriovenous fistula, and other vascular diseases and injuries of the type found in the aorta and aorto-iliac bifurcation of the human anatomy. The graft can be delivered via a catheter delivery system to the site of the disease or injury, where it is assembled and deployed to provide an internal bypass conduit for blood flow through the diseased, injured or otherwise compromised artery. Isolation of the lesion is thereby achieved, eliminating the risk associated with loss of flow path integrity, e.g., rupture of an aneurysm.

The graft is typically made of a plurality of tubular prostheses or thin wall graft members, each of which is constructed using a small support structure and a very thin graft material such as Dacron® or expanded polytetrafluoroethylene (ePTFE). Each component prosthesis or thin wall graft member is nested, laminated or layered in situ to form a completed structurally sound stent-graft. Each component is delivered sequentially, overlapping partially or completely the component or components previously deployed. For bifurcated applications, an initial bifurcated laminate, component or thin wall graft member can be positioned and followed by multiple tubular thin wall graft members into each leg of the original bifurcated graft member. Alternatively, each component or graft member may be of bifurcated construction and be sequentially laminated or deployed in place within a preselected portion of a patient's body lumen or vessel. Progressive overlap of thin wall graft members can be used to traverse preselected portions of a patient's body lumen that have significant angulation so long as there are sufficient layers of thin wall graft member built up over the entire compromised preselected portion of the lumen. For body lumens with high angulation, this method can incorporate the use of thin wall graft members or components having a relatively short longitudinal length so as to decrease the tendency of each graft member to buckle or fold on itself as a result of conforming to the angulation.

The thin wall graft members can contain deformable wire at their proximal and distal ends to allow anchoring to the body lumen wall in locations proximal and distal the compromised or diseased portion of the body lumen. The deformable wire portions or anchoring mechanisms can be used to secure the graft to the lumen wall of the patient, or to secure the thin wall graft members to each other. The deformable wires can be self expanding from a constrained state or balloon expandable. In addition to the deformable wires, adjacent thin wall graft members can be secured to each other or the lumen wall with hooks or suitable polymer adhesives, such as cyanoacrylate compounds. Size differences between the various graft members that make up a graft can be determined by specific materials, architectures and applications. Each graft member can have radiopaque markers or materials to facilitate imaging of the graft members during delivery and deployment. The number, size and shape of the thin wall graft members can be selected from a standard set or adjusted so as to allow tailoring of the final device shape to a patient's specific anatomy, and can be defined with the assistance of a flouroscopic imaging, spiral CT angiography or MRI.

The nested or layered approach to deploying the thin wall graft members described herein will allow each member to be smaller, more flexible, and have a lower profile than would a single element device typically used to treat the same body lumen. While each individual graft member may lack the necessary mechanical characteristics or properties of a completed graft or device, the aggregate assembly of all of the components in situ will achieve the required structural objectives. These objectives include strength, stiffness, and non-porosity necessary for device patency, hemodynamic sealing, and prevention of perigraft leakage. This approach will allow for improved percutaneous delivery through a delivery catheter system to preselected portions of a body lumen using smaller diameter delivery catheters than those typically used.

A nested or layered approach used for deploying tubular members can also be used for treatment of occlusive disease using stents and stent-grafts. A series of concentric stents that converge concentrically into position for deployment can be used to achieve similar benefits of delivery flexibility and low profile. During delivery the stent components would be extended linearly in telescopic fashion within a delivery catheter, with each successive component or stent member sized to fit inside the adjacent stent member or component. Once the leading end of the series of components of stent members reaches a preselected lesion site within a patient's body lumen, the remaining stent members or components are moved into position for deployment and completion and consolidation of the device.

Figure 2:
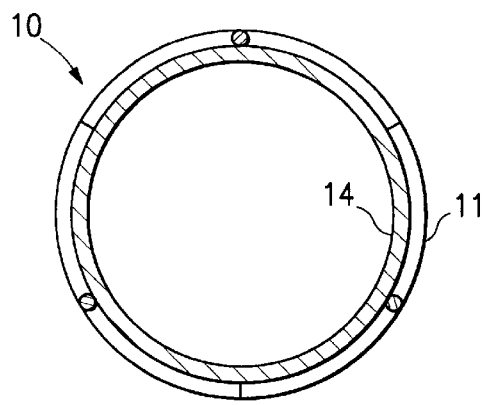
FIG. 2 shows a transverse cross section of the endovascular graft of FIG. 1 taken at lines 2—2 of FIG. 1.
Figure 3:
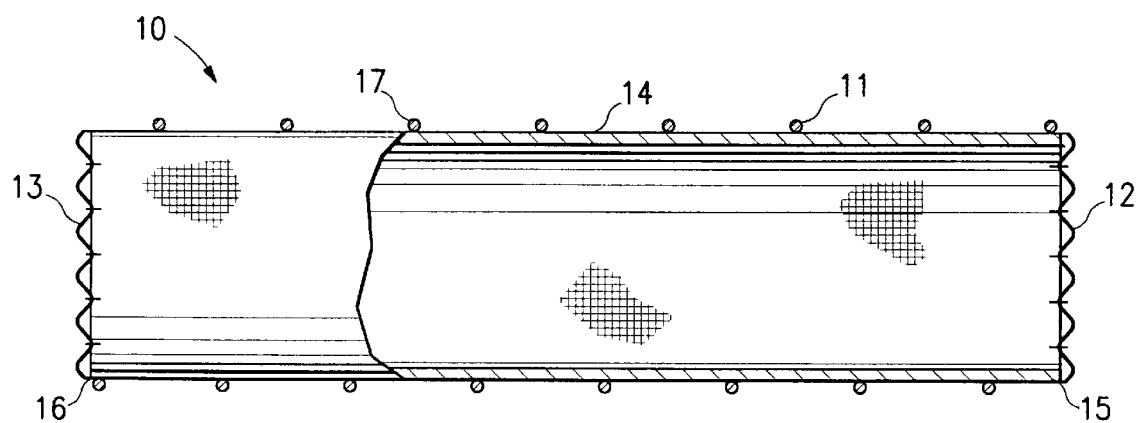
FIG. 3 shows a longitudinal cross sectional view of the endovascular graft of FIG. 1 taken at lines 3—3 of FIG. 1.

Referring to FIG. 1, a thin wall graft member 10 is shown having a frame 11, a first anchoring mechanism 12, a second anchoring mechanism 13, and a tubular membrane 14 disposed within and secured to the frame. FIG. 2 shows a transverse cross section of the thin wall graft member 10 of FIG. 1 with the membrane 14 disposed within and secured to the frame 11. FIG. 3 is a longitudinal cross section of the thin wall graft member 10 of FIG. 1 with the membrane 14 disposed within the frame 11 and first anchoring mechanism 12 disposed at a first end 15 of the member and a second anchoring mechanism 13 disposed at a second end 16 of the member.

The graft can be configured so that no single component or thin wall graft member has sufficient mechanical strength to provide a desired amount of support for a preselected length of a patient's body lumen. The thin wall graft members can be designed so that a desired amount of mechanical strength can be achieved with two or more layers or overlapped portions of the graft. In some indications, it may be desirable to have three, four, five or more layers required to achieve the desired amount of mechanical strength and support for the patient's body lumen. The frame 11 is made from an expandable wire 17, preferably a pseudoelastic alloy such as nickel titanium (NiTi), but can also be made from a high strength material such as stainless steel or Co—Cr—Ni alloys such as MP35N and the like. The material of the frame has a diameter or transverse dimension of about 0.010 inches, but can be from about 0.005 to about 0.016 inches. The first anchoring mechanism and second anchoring mechanism 13 are made of materials similar to those of the frame. The anchoring mechanisms 12 and 13 are of nickel titanium (NiTi) having a transverse dimension of about 0.01 inches, but can be from about 0.005 to about 0.016 inches in transverse dimension. Although the thin wall graft member 10 is shown with a frame 11, the graft member can be constructed without the frame and be supported by anchoring mechanisms 12 and 13 alone.

The membrane 14 is preferably made from Dacron® or ePTFE fabric but can be of any other suitable thin material that can impede the flow of blood or other bodily fluids. Additional suitable materials can include polyurethane, polyvinylchloride, polyethylene terephthalate (PET), polyetheretherkeyton (PEEK) and the like. The thickness of the membrane 14 is about 0.004 inches, but can be from about 0.002 to about 0.008 inches.

The thin wall graft member 10 is generally longer than the compromised tissue or aneurysm of the patient's body lumen, and is about 6 to about 20 cm, preferably about 8 to about 12 cm. The transverse dimension of the thin wall graft member is about 15 to about 40 mm, preferably about 20 to about 35 mm. Although the maximum transverse dimension of the graft member 10 is as described above, the graft member can be expanded or self expanding to any size up to the maximum transverse dimension and engage a lumen wall in which the graft member is being deployed. The graft member 10 will generally be sized to have a slightly larger maximum transverse dimension than the transverse dimension of the vessel or lumen within which it is to be deployed. This allows for the anchoring mechanisms 12 and 13 and frame 11 to engage the inside surface of the body lumen and be secured and at least partially sealed thereto.

The graft member 10 is compressible or constrainable to a smaller transverse dimension for loading into a delivery catheter system. The smallest transverse dimension that the graft member 10 can be constrained to for loading and delivery into and out of a suitable delivery catheter is the minimum transverse dimension. The minimum transverse dimension of the graft member 10 in a constrained state is about 4 mm, but can be up to about 6 mm. Preferably, the minimum transverse dimension of the graft member is about 2 to about 4 mm.

Figure 4:
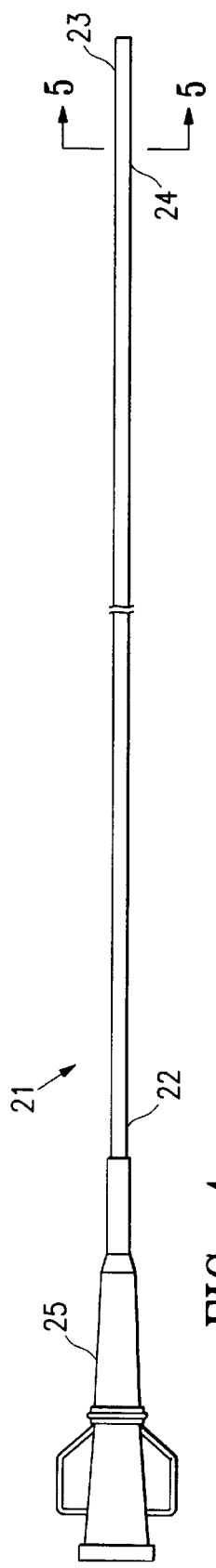
FIG. 4 is an elevational view of a catheter delivery system suitable for delivery of a graft having features of the invention.
Figure 5:
FIG. 5 is a transverse cross sectional view of the catheter delivery system of FIG. 4 taken at lines 5—5 in FIG. 4.

FIG. 4 is an elevational view of a delivery catheter 21 having a proximal end 22, a distal end 23, and a distal section 24. Luer connector 25 is disposed at the proximal end 22 of the delivery catheter. The delivery catheter 21 is constructed using common guiding or delivery catheter methods and can be of a solid polymer material or optionally can have a mesh, coil or braid of a suitable high strength metal or fiber embedded therein. FIG. 5 is a transverse cross sectional view of the delivery catheter 21 shown in FIG. 4 taken at lines 5—5 in FIG. 4 at the distal section 24 of the delivery catheter. The delivery catheter 21 has a lumen 26 extending the length of the catheter which has an inner diameter of about 4 to about 5 mm. The wall 27 of the distal section 24 has a thickness of about 0.01 inches, but can have a thickness of about 0.005 to about 0.05 inches. The length of the delivery catheter 21 is about 20 to about 50 cm, but can be about 10 to about 150 cm. The delivery catheter 21 preferably has a low friction surface inside the lumen to facilitate deployment of thin wall graft members. The wall 27 of the delivery catheter 21 is shown as having a single polymer layer, but may be constructed of multiple concentric or eccentric layers, preferably with the inner-most layer being of a low friction polymer such as TFE or high density polypropylene. Other suitable polymers for the delivery catheter 21 include polyurethane, polyvinylchloride, polyimide, polyamide and the like. The delivery catheter 21 may also optionally have more than one lumen, including a lumen for passage of a guidewire or similar device.

Figure 6:
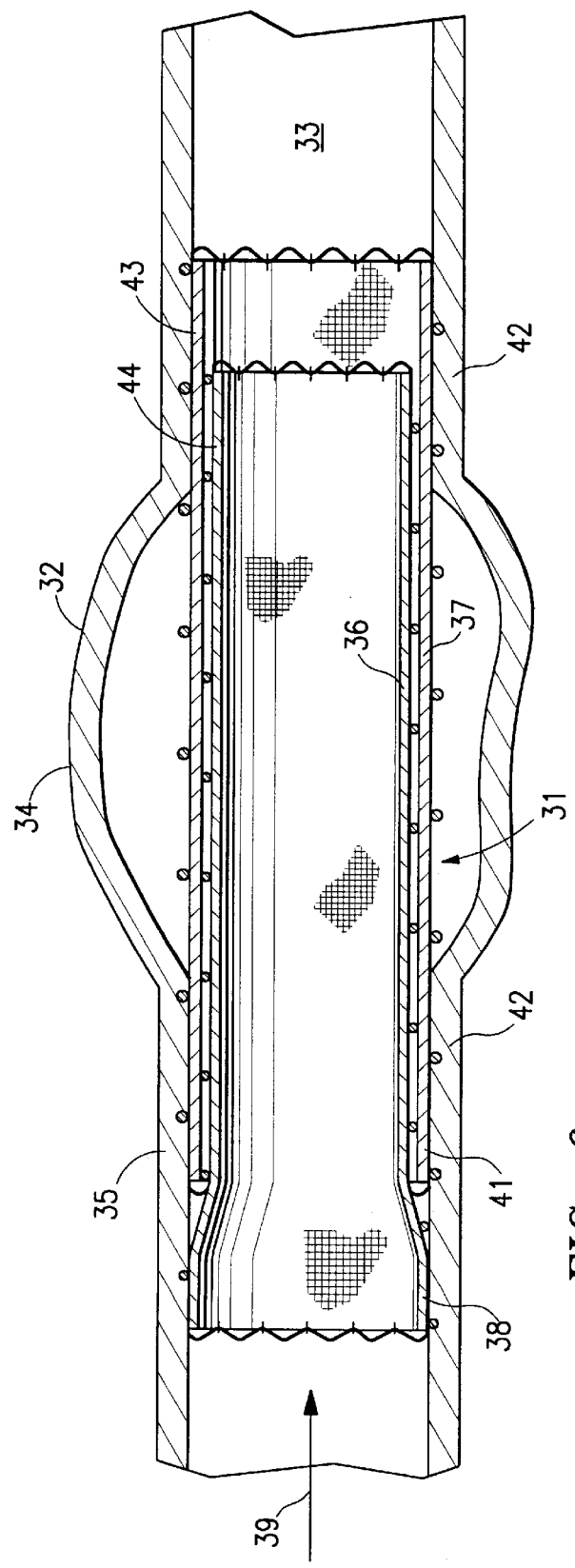
FIG. 6 is a longitudinal cross sectional view of a graft having features of the invention deployed in a patient's body lumen.

FIG. 6 shows a graft 31 having features of the invention deployed within a preselected portion 32 of a patient's body lumen 33. The preselected portion 32 of the patient's body lumen 33 has a distended portion 34 that is representative of an aortic aneurysm or the like. The body lumen 33 has a wall 35 that is engaged by the graft 31. A second or inner-most thin wall graft member 36 is disposed and deployed within a first thin wall graft member 37. A first end 38 of the second thin wall graft member 36 is extending longitudinally from a first end 41 of the first thin wall graft member 37 to provide a smooth transition for a flow of blood therethrough as indicated by arrow 39. Both the first and second thin wall graft members 36 and 37 completely span the preselected portion 32 of the patient's body lumen. The first end 41 of the first thin wall graft member 37 and the first end 38 of the second thin wall graft member are secured to a healthy tissue portion 42 of the body lumen 33. A second end 43 of the first thin wall graft member 37 and a second end 44 of the second thin wall graft member 36 are also secured to a healthy tissue portion 42 of the body lumen. Although the healthy tissue portion 42 of the patient's body lumen 33 is shown as having a constant diameter in FIG. 6, the term healthy tissue portion or is intended to mean any portion of a patient's body lumen or passageway that has sufficient strength or integrity to support an anchoring mechanism 12 and 13 of the type discussed herein above.

Figure 7:
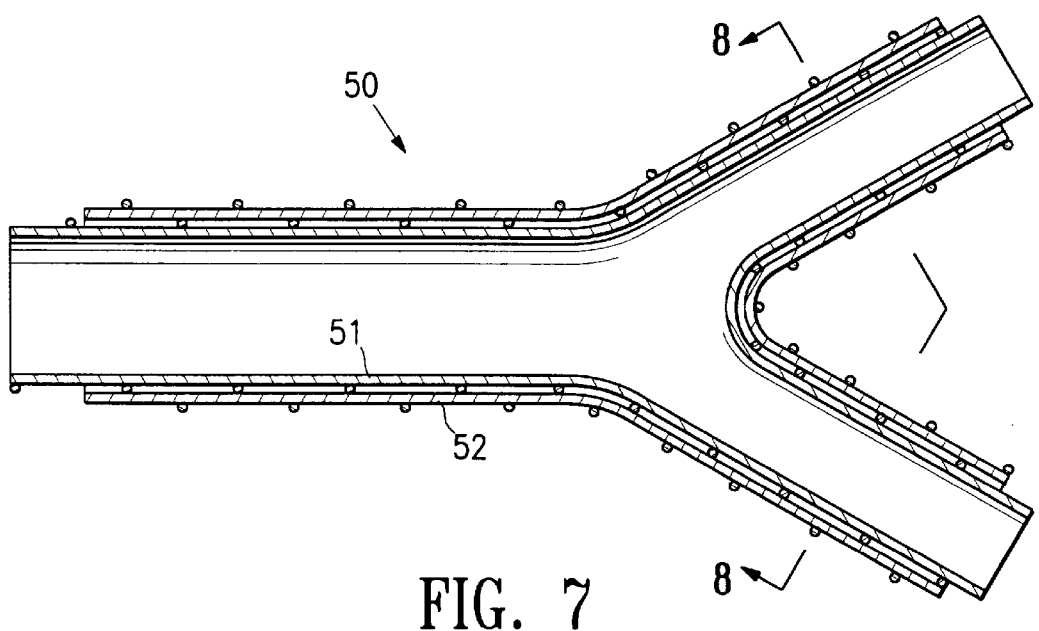
FIG. 7 is an elevational view in section of a bifurcated embodiment of a graft having features of the invention.

FIG. 7 is an elevational view of a bifurcated embodiment of a graft 50 having features of the invention shown in an expanded deployed state. A second thin wall graft member 51 is disposed within a first thin wall graft member 52. The first thin wall graft member 51 and the second thin wall graft member 52 each has a bifurcated configuration and a construction similar to that of the of the thin wall graft of FIGS. 1–3.

Figure 8:
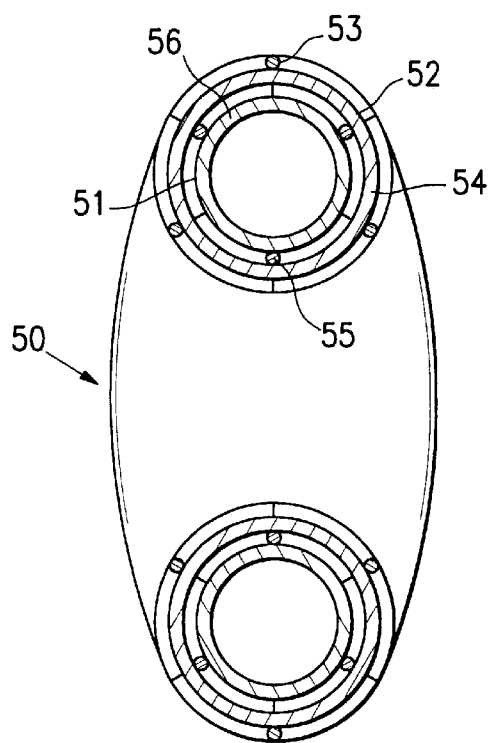
FIG. 8 is a transverse cross sectional view of the endovascular graft of FIG. 7 taken at lines 8—8 of FIG. 7.

FIG. 8 is a transverse cross sectional view of the graft 50 of FIG. 7 taken at lines 8—8 of FIG. 7. The first thin wall graft member 52 is bifurcated and has a frame 53 and a membrane 54 within the frame. The second thin wall graft member 51 is disposed within the first thin wall graft member 52 and has a frame 55 and a membrane 56 within the frame. The cross section of the first thin wall member 52 and second thin wall member 51 is shown as round, but is sufficiently flexible to assume a variety of shapes necessary to engage an inside surface of a body lumen, including irregularly shaped body lumens. In addition, although the graft 50 of FIG. 7 is shown with two thin wall graft members 51 and 52, any suitable number of graft members could be used, so long as all portions of the graft 50 which span a preselected length of the patient's body lumen which is compromised have a sufficient number of graft member layers and structural strength to maintain a flow of blood therethrough and prevent leakage or failure of the patient's body lumen. The thin wall graft members 51 and 52 of FIG. 7 are shown as complete bifurcated embodiments, however, they may optionally be formed from multiple overlapping thin wall graft members that are individually either partially bifurcated or not bifurcated at all.

What is claimed is:

1. An endovascular graft adequate for maintaining a flow of blood therethrough and preventing leakage or failure of a compromised portion of a patient's body lumen comprising a plurality of individually deliverable thin wall graft members layered in a deployed state with at least two layers of thin wall graft member present across an entire length of the compromised portion of the patient's body lumen.

2. The endovascular graft of claim 1 wherein no single thin wall graft member in a deployed state is sufficient to adequately maintain a flow of blood therethrough and prevent leakage or failure of the patient's body lumen for the compromised portion of the patient's body lumen.

3. The endovascular graft of claim 1 wherein at least one of the thin wall graft members is shorter than the entire length of the compromised portion of the patient's body lumen and is axially overlapped and combined with at least one other thin wall graft member so that the combination of thin wall graft members extends across the entire length of the compromised portion of the patient's body lumen.

4. The endovascular graft of claim 1 wherein all of the thin wall graft members are shorter than the entire length of the compromised portion of the patient's body lumen and are axially overlapped in layers to provide at least two layers of thin wall graft member present across the entire length of the compromised portion of the patient's body lumen.

5. The endovascular graft of claim 1 wherein the graft comprises at least 3 thin wall graft members and all of the thin wall graft members are overlapped.

6. The endovascular graft of claim 1 wherein an inner most thin wall graft member has an axial length substantially greater than all other thin wall graft members such that the inner most thin wall graft member extends longitudinally beyond a distal end and a proximal end of all other thin wall graft members when deployed.

7. The endovascular graft of claim 1 wherein the thin wall graft members are configured to be expanded to a transverse dimension of up to about 40 mm and constrained to a maximum outer transverse dimension of down to about 3 mm.

8. The endovascular graft of claim 1 wherein each thin wall graft member further comprises an anchoring mechanism at both ends and at least two of the thin wall graft members have a longitudinal length sufficient to span the entire length of the compromised portion of the patient's body lumen and engage tissue of sufficient integrity to support the anchoring mechanisms at the both ends of the at least two thin wall graft members.

9. A method of deploying an endovascular graft adequate for maintaining a flow of blood therethrough and preventing leakage or failure of a compromised portion of a patient's body lumen within the patient's body lumen, comprising:
   a) providing an endovascular graft comprising at least two thin wall graft members configured to be layered in a deployed state;
   b) percutaneously delivering a first thin wall graft member individually through a low profile delivery catheter system to the compromised portion of the patient's body lumen;
   c) percutaneously delivering at least one additional thin wall graft member through a low profile delivery catheter system and positioning the at least one additional thin wall graft member within a longitudinal lumen of the first thin wall graft member so as to at least partially axially overlap the first thin wall graft member; and
   d) deploying the first thin wall graft member and the at least one additional thin wall graft member until the first and at least one additional thin wall graft members are in a desired configuration within the passageway of the patient with at least two layers of thin wall graft member present across an entire length of the compromised portion of the patient's body lumen.

10. The method of claim 11 wherein an inner most thin wall graft member extends longitudinally beyond the other thin wall graft member or members and engages the patient's body lumen directly.

11. The method of claim 9 wherein the compromised portion of the patient's body lumen has a curvature and the thin wall graft members are progressively deployed such that each additional thin wall graft member is offset in the same longitudinal direction through the curvature of the patient's body lumen so that each additional thin wall graft member is sufficiently short in longitudinal length to absorb the curvature of the passageway without kinking.

12. A kit with components suitable for forming an endovascular graft adequate for maintaining a flow of blood therethrough and preventing leakage or failure of a compromised portion of a patient's body lumen comprising a plurality of individually deliverable thin wall graft members configured to be layered in a deployed state with at least two layers of thin wall graft member present across an entire length of the compromised portion of the patient's body lumen.

13. The kit of claim 12 wherein the plurality of thin wall graft members are configured to be deployed within a low profile delivery catheter system.

14. The kit of claim 13 wherein the plurality of thin wall graft members are configured to be delivered through a delivery catheter system with a maximum distal outer transverse dimension of up to about 4 mm.

15. An endovascular graft adequate for maintaining a flow of blood therethrough and preventing leakage or failure of a compromised portion of a patient's body lumen comprising a plurality of thin wall graft members that are linked so as to allow relative longitudinal movement therebetween and that are configured to be layered in a deployed state with at least two layers of thin wall graft member present across an entire length of the compromised portion of the patient's body lumen.

16. The endovascular graft of claim 15 wherein the plurality of thin wall graft members are configured to be telescopically linked to allow for longitudinal extension during delivery and layering in a deployed state.

17. A method of deploying an endovascular graft adequate for maintaining a flow of blood therethrough and preventing leakage or failure of a compromised portion of a patient's body lumen within the patient's body lumen, comprising:
   a) providing an endovascular graft comprising at least two thin wall graft members configured to be layered in a deployed state;
   b) percutaneously delivering a first thin wall graft member through a low profile delivery catherer system to a desired site within the patient's body lumen and deploying the first thin wall graft member axially coextensive with at least a portion of the compromised portion of the patient's body lumen;
   c) percutaneously delivering at least one additional thin wall graft member through a low profile delivery catherer system and positioning the at least one additional thin wall graft member at least partially within a longitudinal lumen of the deployed first thin wall graft member; and
   d) deploying the at least one additional thin wall graft member within the longitudinal lumen of the deployed first thin wall graft member such that there are at least two layers of thin wall graft member present across an entire length of the compromised portion of the patient's body lumen.

18. The method of claim 17 wherein an inner most thin wall graft member extends longitudinally beyond the other thin wall graft members and engages the patient's body lumen directly.

19. An endovascular graft adequate for maintaining a flow of blood therethrough comprising a plurality of separate thin wall graft members having thin graft material supported by and secured to a support structure and the members layered in a deployed state with at least two layers of thin wall graft member present across an entire length of a compromised portion of a patient's body lumen.

20. A method of deploying an endovascular graft adequate for maintaining a flow of blood therethrough within a patient's body lumen, comprising:
   a) providing an endovascular graft comprising at least two thin wall graft members configured to be layered in a deployed state;
   b) percutaneously delivering the at least two thin wall graft members longitudinally extended from each other through a low profile delivery catherer system to a desired site within the patient's body lumen; and
   c) deploying the at least two thin wall graft members such that there are at least two layers of thin wall graft member present across an entire length of a compromised portion of the patient's body lumen.

21. The method of claim 20 wherein at least one thin wall graft member is at least partially deployed within a longitudinal lumen of another thin wall graft member.

22. A method of deploying an endovascular graft adequate for maintaining a flow of blood therethrough, comprising;
   a) providing an endovascular graft comprising at least two thin wall graft members configured to be layered in a deployed state;
   b) percutaneously delivering a first thin wall graft member through a low profile delivery catherer system to a desired site within a patient's body lumen and deploying the first thin wall graft member;
   c) percutaneously delivering at least one additional thin wall graft member to a desired site within the patient's body lumen through a low profile delivery catherer system; and
   d) deploying the at least one additional thin wall graft member such that there are at least two layers of thin wall graft members present across an entire length of a compromised portion of the patient's body lumen.

* * * * *

UNITED STATES PATENT AND TRADEMARK OFFICE
CERTIFICATE OF CORRECTION

PATENT NO. : 6,331,191 B1
DATED : December 18, 2001
INVENTOR(S) : Chobotov, M.

It is certified that error appears in the above-identified patent and that said Letters Patent is hereby corrected as shown below:

<u>Column 8,</u>
Lines 42-45, please replace claim 10 with the following:
-- 10.   The method of claim 9 wherein an inner most thin wall graft member extends longitudinally beyond the other thin wall graft member or members and engages the patient's body lumen directly. --

Signed and Sealed this

Thirteenth Day of August, 2002

Attest:

Attesting Officer

JAMES E. ROGAN
*Director of the United States Patent and Trademark Office*